United States Patent
Bachmann et al.

(10) Patent No.: US 9,394,304 B2
(45) Date of Patent: Jul. 19, 2016

(54) IMIDAZOPYRIDINE DERIVATIVES

(71) Applicant: Hoffmann-La Roche Inc., Little Falls, NJ (US)

(72) Inventors: Stephan Bachmann, Allschwil (CH); Shawn David Erickson, Leonia, NJ (US); Dramane Ibrahim Laine, Hoboken, NJ (US); Yimin Qian, Plainsboro, NJ (US)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 14/712,495

(22) Filed: May 14, 2015

(65) Prior Publication Data
US 2015/0246918 A1 Sep. 3, 2015

Related U.S. Application Data

(63) Continuation of application No. PCT/EP2013/073456, filed on Nov. 11, 2013.

(60) Provisional application No. 61/726,149, filed on Nov. 14, 2013.

(51) Int. Cl.
| C07D 401/02 | (2006.01) |
| C07D 401/10 | (2006.01) |
| A61K 31/437 | (2006.01) |
| A61K 31/4353 | (2006.01) |
| C07D 471/04 | (2006.01) |

(52) U.S. Cl.
CPC .................................. C07D 471/04 (2013.01)

(58) Field of Classification Search
CPC .. C07D 401/02; C07D 401/10; A61K 31/437; A61K 31/4353
USPC .......................................... 546/121; 514/300
See application file for complete search history.

(56) References Cited

U.S. PATENT DOCUMENTS

| 6,703,404 B2 * | 3/2004 | Maul ................... C07D 471/04 514/300 |
| 2004/0058938 A1 * | 3/2004 | Cullmann ............... A01N 43/90 514/259.1 |

FOREIGN PATENT DOCUMENTS

| WO | 01/27111 A2 | 4/2001 |
| WO | 0127119 * | 4/2001 |
| WO | 2007/067711 A2 | 6/2007 |
| WO | 2008/016648 A2 | 2/2008 |
| WO | 2009/061856 A1 | 5/2009 |
| WO | 2010/032195 A1 | 3/2010 |
| WO | 2010/109328 A1 | 9/2010 |
| WO | 2011/006143 A2 | 1/2011 |

OTHER PUBLICATIONS

Varma et al., Tetrahedron Letters (1999), 40(43), 7665-7669.*
Varma et al., Journal of Heterocyclic Chemistry (1999), 36(6), 1565-1571.*
International Preliminary Report on Patentability issued in International Application No. PCT/EP2013/073456, dated Feb. 9, 2015, in 8 pages.
International Search Report issued in International Application No. PCT/EP2013/073456, dated Jan. 8, 2014, in 5 pages.

* cited by examiner

*Primary Examiner* — Niloofar Rahmani
(74) *Attorney, Agent, or Firm* — Lily J. Ackerman

(57) ABSTRACT

The invention is concerned with a compound of formula (I)

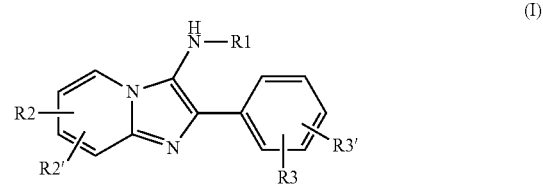

wherein R1, R2, R2', R3, R3' are as defined in the description and in the claims. The compound of formula (I) can be used as a medicament.

8 Claims, No Drawings

IMIDAZOPYRIDINE DERIVATIVES

This application is a continuation of International Application No. PCT/EP2013/073456 having an international filing date of Nov. 11, 2013, the entire contents of which are incorporated herein by reference, and which claims benefit under 35 U.S.C. §119 to U.S. Provisional Patent Application No. 61/726,149 filed Nov. 14, 2012, the entire contents of which are incorporated herein by reference.

The present invention relates to organic compounds useful for therapy and/or prophylaxis in a mammal of an inflammatory disease or disorder, and in particular to substituted imidazopyridine compounds, their manufacture, pharmaceutical compositions containing them and their use as Transient Receptor Potential (TRP) channel antagonists.

The invention relates in particular to a compound of formula (I):

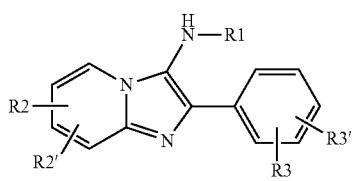

wherein
R1 is lower alkyl, cycloalkyl or —CH₂C(O)OCH₃;
R2 and R2', independently of each other, are hydrogen, halogen, lower alkyl or lower haloalkyl; and
R3 and R3', independently of each other, are hydrogen, halogen, cyano or ethynyl;
or a pharmaceutically acceptable salt thereof.

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor'. Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation.

The invention also provides for pharmaceutical compositions comprising the compounds, methods of using the compounds and methods of preparing the compounds.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1 to R3' of formula (I) refer to moieties that are attached to the core structure of formula (I) by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl. Particular lower alkyls are methyl, ethyl, isopropyl and tert-butyl.

The terms "halo", "halogen" and "halide", which may be used interchangeably, refer to a substituent fluoro, chloro, bromo or iodo. Particular halogens are fluoro, chloro and bromo.

The term "haloalkyl", alone or in combination, denotes an alkyl group substituted with at least one halogen, particularly substituted with one to five halogens, particularly one to three halogens. A particular "haloalkyl" is trifluoromethyl.

"Cycloalkyl" means a monovalent saturated carbocyclic moiety having mono- or bicyclic rings. The cycloalkyl moiety can optionally be substituted with one or more substituents. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof. A particular cycloalkyl is cyclopropyl.

Unless otherwise indicated, the term "hydrogen" or "hydro" refers to the moiety of a hydrogen atom (—H) and not H₂.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula (I) to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula (I) (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glyceryl monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The invention further relates in particular to:

A compound of formula (I) wherein R2 and R2', independently of each other, are hydrogen, halogen, lower alkyl or lower haloalkyl;

A compound according to formula (I), wherein R1 is lower alkyl;

A compound according to formula (I), wherein R1 is ethyl, propyl, t-butyl, —$CH_2C(O)OCH_3$ or cyclopropyl;

A compound according to formula (I), wherein R1 is ethyl or t-butyl;

A compound according to formula (I), wherein R1 is cycloalkyl;

A compound according to formula (I), wherein R1 is cyclopropyl;

A compound according to formula (I), wherein R2 and R2', independently of each other, are hydrogen, bromine, chlorine, fluoride, —CF$_3$ or methyl;

A compound according to formula (I), wherein one of R2 or R2' is hydrogen and the other is bromine, chlorine, fluorine, —CF$_3$ or methyl;

A compound according to formula (I), wherein R3 and R3', independently of each other, are hydrogen, bromine, chlorine, fluorine, cyano or ethynyl; and A compound according to formula (I), wherein one of R3 or R3' is hydrogen and the other is bromine, chlorine, fluorine, cyano or ethynyl.

The invention further relates in particular to a compound of formula (I) selected from:
6-Bromo-2-(3-chloro-phenyl)-imidazo[1,2-a]pyridin-3-yl]-isopropyl-amine;
[6-Chloro-2-(3-chloro-phenyl)-imidazo[1,2-a]pyridin-3-yl]-isopropyl-amine;
[6-Fluoro-2-(3-fluoro-phenyl)-imidazo[1,2-a]pyridin-3-ylamino]-acetic acid methyl ester;
tert-Butyl-[2-(3-fluoro-phenyl)-6-trifluoromethyl-imidazo[1,2-a]pyridin-3-yl]-amine;
3-(3-tert-Butylamino-6-trifluoromethyl-imidazo[1,2-a]pyridin-2-yl)-benzonitrile;
3-(3-tert-Butylamino-6-chloro-imidazo[1,2-a]pyridin-2-yl)-benzonitrile;
[6-Chloro-2-(3-chloro-phenyl)-imidazo[1,2-a]pyridin-3-yl]-cyclopropyl-amine;
[8-Bromo-6-chloro-2-(3-chloro-phenyl)-imidazo[1,2-a]pyridin-3-yl]-tert-butyl-amine;
[6-Bromo-2-(3-chloro-phenyl)-7-methyl-imidazo[1,2-a]pyridin-3-yl]-tert-butyl-amine;
[6-Bromo-2-(3-chloro-phenyl)-8-methyl-imidazo[1,2-a]pyridin-3-yl]-tert-butyl-amine;
tert-Butyl-[2-(3,5-dichloro-phenyl)-6-trifluoromethyl-imidazo[1,2-a]pyridin-3-yl]-amine;
tert-Butyl-[2-(3-ethynyl-phenyl)-6-trifluoromethyl-imidazo[1,2-a]pyridin-3-yl]-amine;
tert-Butyl-[2-(3-chloro-phenyl)-7-trifluoromethyl-imidazo[1,2-a]pyridin-3-yl]-amine;
[2-(3-Chloro-phenyl)-6-trifluoromethyl-imidazo[1,2-a]pyridin-3-yl]-ethyl-amine;
[2-(3-Ethynyl-phenyl)-6-trifluoromethyl-imidazo[1,2-a]pyridin-3-yl]-isopropyl-amine;
[2-(3-Chloro-phenyl)-6-trifluoromethyl-imidazo[1,2-a]pyridin-3-yl]-isopropyl-amine;
[2-(3-Bromo-phenyl)-6-trifluoromethyl-imidazo[1,2-a]pyridin-3-yl]-tert-butyl-amine; or
3-(3-tert-Butylamino-6-fluoro-imidazo[1,2-a]pyridin-2-yl)-benzonitrile.

The invention also relates in particular to a compound of formula (I) selected from
6-Bromo-2-(3-chloro-phenyl)-imidazo[1,2-a]pyridin-3-yl]-isopropyl-amine;
[6-Chloro-2-(3-chloro-phenyl)-imidazo[1,2-a]pyridin-3-yl]-isopropyl-amine;
tert-Butyl-[2-(3-ethynyl-phenyl)-6-trifluoromethyl-imidazo[1,2-a]pyridin-3-yl]-amine;
[2-(3-Ethynyl-phenyl)-6-trifluoromethyl-imidazo[1,2-a]pyridin-3-yl]-isopropyl-amine; and
[2-(3-Chloro-phenyl)-6-trifluoromethyl-imidazo[1,2-a]pyridin-3-yl]-isopropyl-amine.

The invention also relates to:

A pharmaceutical composition comprising a therapeutically effective amount of a compound according to formula (I) and a pharmaceutically acceptable carrier;

A compound according to formula (I) for use as a therapeutically active substance;

A compound according to formula (I) for use as a therapeutically active substance in the treatment or prophylaxis of a respiratory disorder;

The use of a compound according to formula (I) for the preparation of a medicament for the treatment or prophylaxis of a respiratory disorder;

A method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

Examples of respiratory disorders are for example chronic obstructive pulmonary disorder (COPD), asthma, allergic rhinitis and bronchospasm.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in Scheme 1.

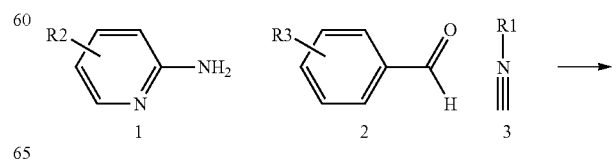

-continued

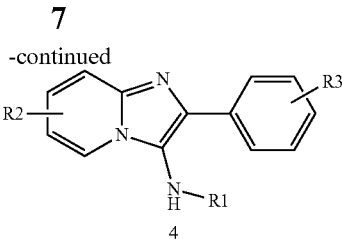

As shown in Scheme 1, the desired imidazolopyridines can be prepared under Groebke-Blackburn-Bienayme reaction conditions. The multiple component reaction (MCR) between substituted 2-aminopyridine (1), substituted benzaldehyde (2) and alkylisocyanide (3) in the presence of acid catalysis, such as p-tolunesulfonic acid, can afford the desired imidazolopyridine analogs (4).

The invention also relates to a process for the manufacture of a compound of formula (I) comprising the reaction of a compound of formula (A)

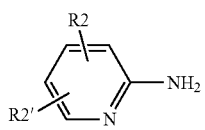

in the presence of a compound of formula (B)

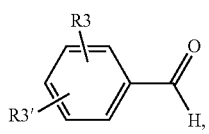

a compound of formula (C)

and an acid, wherein R1 to R3' are as defined above.

The acid of the above process can be for example p-tolunesulfonic acid. Said acid can be used for example in catalytic quantities.

The invention also relates to a compound according of formula (I) manufactured according to the process of the invention.

The invention will now be illustrated by the following examples which have no limiting character.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep $C_{18}$ column (5 μm, OBD™ 20×100 mm) from Waters Corporation, or a SunFire™ Prep $C_{18}$ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex®II FTICR with a 4.7 Tesla magnet (from Bruker Corporation), a Waters® Alliance® 2795-ZQ™2000 (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.

Absolute stereochemistry, where assigned, is based on comparison of biological potency and/or relative retention time on silica gel TLC and chromatography to analogs prepared from chiral building blocks of known absolute configuration.

Example 1

6-Bromo-2-(3-chloro-phenyl)-imidazo[1,2-a]pyridin-3-yl]-isopropyl-amine

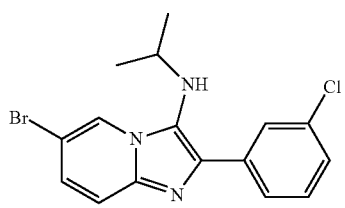 [SMILES: CC(C)Nc1c(-c2cccc(Cl)c2)nc2ccc(Br)cn12]

5-Bromopyridin-2-amine (340 mg, 1.97 mmol), 3-chlorobenzaldehyde (290 mg, 2.06 mmol), and p-toluenesulfonic acid monohydrate (110 mg, 0.58 mmol) were combined in 3 mL of methanol. To this solution was added 2-isocyanopropane (140 mg, 2.03 mmol). The resulting green solution (clear) was stirred at room temperature for 1.5 h. The mixture was filtered and the solid was rinsed with dry methanol three times to give an off white solid as 6-bromo-2-(3-chloro-phenyl)-imidazo[1,2-a]pyridin-3-yl]-isopropyl-amine (318 mg, 44.4%). MS: 365.8 [M+H]$^+$; $^1$H-NMR (DMSO-d$_6$): δ 8.59 (s, 1H), 8.23 (s, 1H), 8.13 (d, 1H), 7.45 (m, 2H), 7.32 (m, 2H), 4.91 (d, 1H), 3.20 (m, 1H), 1.04 (d, 6H).

Example 2

[6-Chloro-2-(3-chloro-phenyl)-imidazo[1,2-a]pyridin-3-yl]-isopropyl-amine

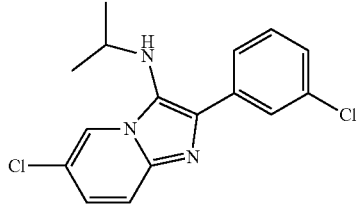 [SMILES: CC(C)Nc1c(-c2cccc(Cl)c2)nc2ccc(Cl)cn12]

5-Chloropyridin-2-amine (130 mg, 1.01 mmol), 3-chlorobenzaldehyde (171 mg, 1.21 mmol) and p-toluenesulfonic acid monohydrate (77 mg, 0.40 mmol) were combined in 2 mL of methanol to give a clear solution. To this solution was added 2-isocyanopropane (78 mg, 1.13 mmol) and the resulting clear solution was stirred at room temperature for 45 minutes. The mixture was filtered and the white solid was rinsed with methanol three times. The white solid was dried to afford [6-chloro-2-(3-chloro-phenyl)-imidazo[1,2-a]pyridin-3-yl]-isopropyl-amine (48 mg, 15%). MS: 320.0 and 322.0 [M+H]+; 1H-NMR (DMSO-d6): δ 8.53 (s, 1H), 8.23 (s, 1H), 8.13 (d, 1H), 7.52 (d, 1H), 7.46 (t, 1H), 7.32 (d, 1H), 7.20 (d, 1H), 4.92 (d, 1H), 3.20 (m, 1H), 1.04 (d, 6H).

Example 3

[6-Fluoro-2-(3-fluoro-phenyl)-imidazo[1,2-a]pyridin-3-ylamino]-acetic acid methyl ester

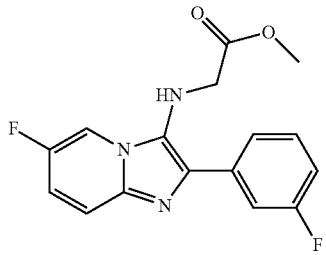 [SMILES: COC(=O)CNc1c(-c2cccc(F)c2)nc2ccc(F)cn12]

5-Fluoropyridin-2-amine (200 mg, 1.78 mmol, Eq: 1.00), 3-fluorobenzaldehyde (240 mg, 205 μL, 1.87 mmol, Eq: 1.05) and p-toluenesulfonic acid monohydrate (102 mg, 535 μmol, Eq: 0.3) were dissolved in MeOH (2.5 mL) and the yellow solution was stirred for 10 min. To this yellow solution was added dropwise methyl 2-isocyanoacetate (182 mg, 167 μL, 1.78 mmol, Eq: 1.00) and the corresponding brown solution was stirred for 90 min. Hexane (2 mL) was added and the solvent was removed to give a beige gummy residue. To this residue, MeOH (2 mL) was added and the precipitate was filtered off, washed with MeOH (4 mL) and dried under vacuum to give the product as an off-white solid (172 mg, 30.4%). MS: 318.2 [M+H]+; 1H-NMR (CDCl3): δ 8.23 (m, 1H), 7.78-7.75 (m, 2H), 7.54 (m, 1H), 7.43 (m, 1H), 7.15-7.00 (m, 2H), 3.84 (d, 2H), 3.77 (s, 3H), 3.73 (m, 1H).

Example 4 tert-Butyl-[2-(3-fluoro-phenyl)-6-trifluoromethyl-imidazo[1,2-a]pyridin-3-yl]-amine

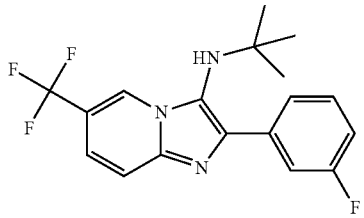 [SMILES: CC(C)(C)Nc1c(-c2cccc(F)c2)nc2ccc(C(F)(F)F)cn12]

5-(trifluoromethyl)pyridin-2-amine (200 mg, 1.23 mmol, Eq: 1.00), 3-fluorobenzaldehyde (161 mg, 137 μl, 1.3 mmol, Eq: 1.05) and p-toluenesulfonic acid monohydrate (70.4 mg, 370 μmol, Eq: 0.3) were dissolved in MeOH (2.00 mL) and the intensive yellow solution was stirred for 20 min. To this yellow solution was added dropwise 2-isocyano-2-methylpropane (103 mg, 140 μl, 1.23 mmol, Eq: 1.00) and the corresponding light yellow solution was stirred for 90 min. The solvent was removed, the remaining solid was treated with MeOH, the precipitate was filtered off, washed with MeOH (2 mL) and dried under vacuum to give the product as a white solid (42 mg, 9.7%). MS: 352.2 [M+H]+; 1H-NMR (CDCl3): δ 8.53 (s, 1H), 7.67-7.53 (m, 3H), 7.35 (m, 1H), 7.24 (dd, 1H), 6.98 (ddd, 1H), 3.06 (s, 1H), 1.01 (s, 9H).

Example 5

3-(3-tert-Butylamino-6-trifluoromethyl-imidazo[1,2-a]pyridin-2-yl)-benzonitrile

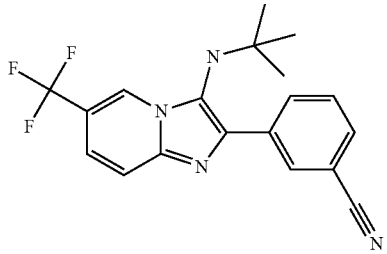 [SMILES: CC(C)(C)Nc1c(-c2cccc(C#N)c2)nc2ccc(C(F)(F)F)cn12]

5-(trifluoromethyl)pyridin-2-amine (200 mg, 1.23 mmol, Eq: 1.00), 3-formylbenzonitrile (170 mg, 1.3 mmol, Eq: 1.05) and p-toluenesulfonic acid monohydrate (70.4 mg, 370 μmol, Eq: 0.3) were dissolved in MeOH (2.00 mL) and the intensive yellow solution was stirred for 20 min. To this yellow solution was added dropwise 2-isocyano-2-methylpropane (103 mg, 140 μL, 1.23 mmol, Eq: 1.00) and the corresponding yellow solution was stirred for 1 h whereupon a white precipitate was formed. The precipitate was filtered off, washed with MeOH (4 mL) and dried under vacuum to give the product as an off-white solid (120 mg, 27.1%). MS: 359.2 [M+H]+;

¹H-NMR (D₆-DMSO): δ 8.91 (s, 1H), 8.64 (s, 1H), 8.54 (d, 1H), 7.81 (d, 1H), 7.74 (d, 1H), 7.68 (t, 1H), 7.48 (dd, 1H), 5.03 (s, 1H), 1.03 (s, 9H).

Example 6

3-(3-tert-Butylamino-6-chloro-imidazo[1,2-a]pyridin-2-yl)-benzonitrile

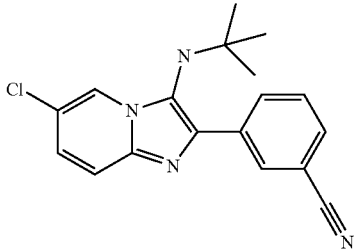 [SMILES: CC(C)(C)Nc1c(-c2cccc(C#N)c2)nc2ccc(Cl)cn12]

5-chloropyridin-2-amine (200 mg, 1.56 mmol, Eq: 1.00), 3-formylbenzonitrile (214 mg, 1.63 mmol, Eq: 1.05) and p-toluenesulfonic acid monohydrate (88.8 mg, 467 µmol, Eq: 0.3) were dissolved in MeOH (2.00 mL) and the intensive yellow solution was stirred for 10 min. To this yellow solution was added dropwise 2-isocyano-2-methylpropane (129 mg, 177 µL, 1.56 mmol, Eq: 1.00) and the corresponding yellow solution was stirred for 80 min whereupon a white precipitate was formed. The precipitate was filtered off, washed with MeOH (4 mL) and dried under vacuum to give the product as a white solid (351 mg, 69.5%). MS: 325.2 [M+H]⁺; ¹H-NMR (D₆-DMSO): δ 8.59 (m, 2H), 8.49 (d, 1H), 7.78 (d, 1H), 7.65 (t, 1H), 7.58 (d, 1H), 7.29 (dd, 1H), 4.88 (s, 1H), 1.02 (s, 9H).

Example 7

[6-Chloro-2-(3-chloro-phenyl)-imidazo[1,2-a]pyridin-3-yl]-cyclopropyl-amine

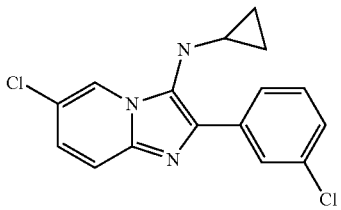 [SMILES: Clc1cccc(-c2nc3ccc(Cl)cn3c2NC2CC2)c1]

5-chloropyridin-2-amine (100 mg, 778 µmol, Eq: 1.00), 3-chlorobenzaldehyde (115 mg, 93.0 µl, 817 µmol, Eq: 1.05) and p-toluenesulfonic acid monohydrate (44.4 mg, 233 µmol, Eq: 0.3) were dissolved in MeOH (1.00 mL) and the intensive yellow solution was stirred for 10 min. To this yellow solution was added dropwise isocyanocyclopropane (52.2 mg, 47.4 µL, 778 µmol, Eq: 1.00) and the corresponding yellow solution was stirred for 2 h. The solvent was removed and the dark red oil was purified twice by flash column chromatography (ethyl acetate in hexanes) to give the product as yellow solid (45 mg, 18.2%). LC/MS (acid polar): 318.1 [M+H]⁺; ¹H-NMR (CDCl₃): δ 8.50 (s, 1H), 8.21 (s, 1H), 8.14 (d, 1H), 7.58 (d, 1H), 7.49 (t, 1H), 7.38 (d, 1H), 7.28 (d, 1H), 5.44 (s, 1H), 2.70 (m, 1H), 0.46-0.39 (m, 4H).

Example 8

[8-Bromo-6-chloro-2-(3-chloro-phenyl)-imidazo[1,2-a]pyridin-3-yl]-tert-butyl-amine

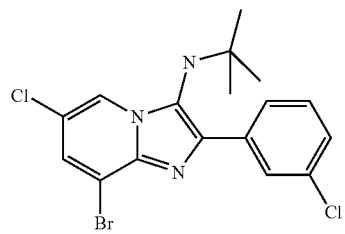 [SMILES: CC(C)(C)Nc1c(-c2cccc(Cl)c2)nc2c(Br)cc(Cl)cn12]

3-bromo-5-chloropyridin-2-amine (200 mg, 964 µmol, Eq: 1.00), 3-chlorobenzaldehyde (142 mg, 115 µl, 1.01 mmol, Eq: 1.05) and p-toluenesulfonic acid monohydrate (55.0 mg, 289 µmol, Eq: 0.3) were dissolved in MeOH (1.5 mL) and the intensive yellow solution was stirred for 5 min. To this yellow solution was added dropwise 2-isocyano-2-methylpropane (80.1 mg, 110 µL, 964 µmol, Eq: 1.00) and the corresponding yellow solution was stirred for 3 h. The solvent was removed and the oily residue was treated with dichloromethane and filtered over a cartridge. Two fractions were taken. From fraction 1 the product crystallized after treatment with DMSO-d₆. The crystals were filtered off, washed with water and dried under high vacuum to yield the product (48 mg, 12.1%). LC/MS (acid polar): 413.0 [M]⁺; ¹H-NMR (CDCl₃): δ 8.62 (s, 1H), 8.26 (s, 1H), 8.17 (d, 1H), 7.65 (s, 1H), 7.43 (t, 1H), 7.34 (d, 1H), 4.91 (s, 1H), 1.03 (s, 9H).

Example 9

[6-Bromo-2-(3-chloro-phenyl)-7-methyl-imidazo[1,2-a]pyridin-3-yl]-tert-butyl-amine

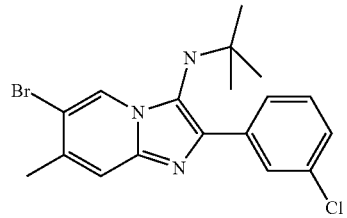 [SMILES: Cc1cc2nc(-c3cccc(Cl)c3)c(NC(C)(C)C)n2cc1Br]

5-bromo-4-methylpyridin-2-amine (200 mg, 1.07 mmol, Eq: 1.00), 3-chlorobenzaldehyde (158 mg, 128 µl, 1.12 mmol, Eq: 1.05) and p-toluenesulfonic acid monohydrate (61.0 mg, 321 µmol, Eq: 0.3) were dissolved in MeOH (1.5 mL) and the intensive yellow solution was stirred for 5 min. To this yellow solution was added dropwise 2-isocyano-2-methylpropane (88.9 mg, 122 µL, 1.07 mmol, Eq: 1.00) and the corresponding yellow solution was stirred for 3 h. To the reaction solution was added water dropwise, leading to a milky suspension (product oiled out). The water/MeOH phase was removed and the oily residue was treated with MeOH (1 mL) and dropwise addition of water. Again a milky suspension was formed and the product oiled out. Upon standing for an hour crystals formed from the oily phase. The crystals were filtered off and washed with water and MeOH, dried under high vacuum to yield the product (148 mg, 35.2%). MS: 394.1 [M+H]$^+$; $^1$H-NMR (D$_6$-DMSO): δ 8.62 (s, 1H), 8.27 (s, 1H), 8.16 (d, 1H), 7.51 (s, 1H), 7.44 (t, 1H), 7.34 (d, 1H), 4.77 (s, 1H), 2.40 (s, 3H), 1.03 (s, 9H).

Example 10

[6-Bromo-2-(3-chloro-phenyl)-8-methyl-imidazo[1,2-a]pyridin-3-yl]-tert-butyl-amine

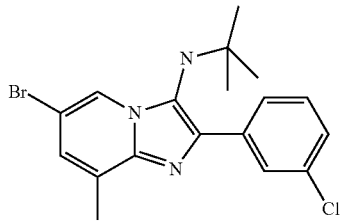 [SMILES: Cc1cc(Br)cn2c(NC(C)(C)C)c(-c3cccc(Cl)c3)nc12]

5-bromo-3-methylpyridin-2-amine (200 mg, 1.07 mmol, Eq: 1.00), 3-chlorobenzaldehyde (158 mg, 128 μL, 1.12 mmol, Eq: 1.05) and p-toluenesulfonic acid monohydrate (61.0 mg, 321 μmol, Eq: 0.3) were dissolved in MeOH (1.5 mL) and the intensive yellow solution was stirred for 5 min. To this yellow solution was added dropwise 2-isocyano-2-methylpropane (88.9 mg, 122 μL, 1.07 mmol, Eq: 1.00) and the corresponding yellow solution was stirred for 2 h. The precipitate was filtered off, washed with MeOH (4 mL) and dried under vacuum to give the product as a white solid (130 mg, 31.0%). MS: 394.1 [M+H]$^+$; $^1$H-NMR (D$_6$-DMSO): δ 8.48 (s, 1H), 8.27 (s, 1H), 8.17 (d, 1H), 7.46 (t, 1H), 7.36 (d, 1H), 7.22 (s, 1H), 4.81 (s, 1H), 3.34 (s, 3H), 1.03 (s, 9H).

Example 11 tert-Butyl-[2-(3,5-dichloro-phenyl)-6-trifluoromethyl-imidazo[1,2-a]pyridin-3-yl]-amine

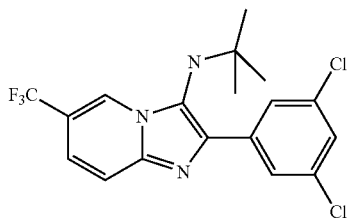 [SMILES: CC(C)(C)Nc1c(-c2cc(Cl)cc(Cl)c2)nc2ccc(C(F)(F)F)cn12]

5-(trifluoromethyl)pyridin-2-amine (200 mg, 1.23 mmol, Eq: 1.00), 3,5-dichlorobenzaldehyde (227 mg, 1.3 mmol, Eq: 1.05) and p-toluenesulfonic acid monohydrate (70.4 mg, 370 μmol, Eq: 0.3) were dissolved in MeOH (1.5 mL). The resulting colorless solution was stirred at rt. To this solution was added dropwise 2-isocyano-2-methylpropane (103 mg, 140 μL, 1.23 mmol, Eq: 1.00) and the corresponding yellow solution was stirred for 2 h. To the yellow clear solution was added dropwise water until the mixture got turbid. After stirring for a few additional minutes, the product precipitated. The solid was filtered off, washed with MeOH/water (1:1) and with hexane and the crystals were dried under vacuum to yield a white solid (231 mg, 46.5%). MS: 402 [M]$^+$; $^1$H-NMR (D$_6$-DMSO): δ 8.91 (s, 1H), 8.30 (d, 2H), 7.73 (d, 1H), 7.57 (t, 1H), 7.49 (d, 1H), 5.05 (s, 1H), 1.07 (s, 9H).

Example 12 tert-Butyl-[2-(3-ethynyl-phenyl)-6-trifluoromethyl-imidazo[1,2-a]pyridin-3-yl]-amine

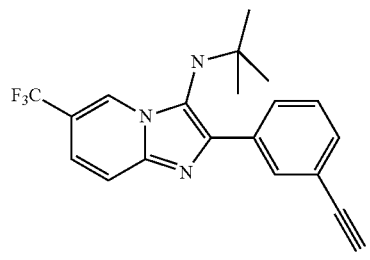 [SMILES: C#Cc1cccc(-c2nc3ccc(C(F)(F)F)cn3c2NC(C)(C)C)c1]

5-(trifluoromethyl)pyridin-2-amine (100 mg, 617 μmol, Eq: 1.00), 3-ethynylbenzaldehyde (84.3 mg, 648 μmol, Eq: 1.05) and p-toluenesulfonic acid monohydrate (35.2 mg, 185 μmol, Eq: 0.3) were dissolved in MeOH (1.00 mL) and the intensive yellow solution was stirred for 5 min. To this yellow solution was added dropwise 2-isocyano-2-methylpropane (51.3 mg, 70.2 μL, 617 μmol, Eq: 1.00) and the corresponding yellow solution was stirred for 2 h. Water was added, the oil was separated from water/MeOH phase and purified by flash column chromatography (40 g SiO$_2$, Hex/EtOAc 100:0 to 0:100) to yield a yellow solid (120 mg, 54.4%). MS: 357.0 [M]$^+$; $^1$H-NMR (D$_6$-DMSO): δ 8.89 (s, 1H), 8.38 (s, 1H), 8.27 (d, 1H), 7.72 (d, 1H), 7.52-7.40 (m, 3H), 4.94 (s, 1H), 4.22 (s, 1H), 1.04 (s, 9H).

Example 13 tert-Butyl-[2-(3-chloro-phenyl)-7-trifluoromethyl-imidazo[1,2-a]pyridin-3-yl]-amine

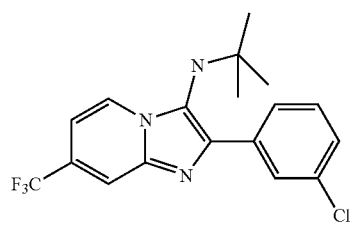 [SMILES: CC(C)(C)Nc1c(-c2cccc(Cl)c2)nc2cc(C(F)(F)F)ccn12]

4-(trifluoromethyl)pyridin-2-amine (200 mg, 1.23 mmol, Eq: 1.00), 3-chlorobenzaldehyde (182 mg, 147 μl, 1.3 mmol, Eq: 1.05) and p-toluenesulfonic acid monohydrate (70.4 mg, 370 Eq: 0.3) were dissolved in MeOH (2.00 mL). The resulting colorless solution was stirred at rt. To this solution was added dropwise 2-isocyano-2-methylpropane (103 mg, 140 μL, 1.23 mmol, Eq: 1.00) and the corresponding yellow solution was stirred for 2 h. To the yellow clear solution was added dropwise water until the mixture got turbid and the product precipitated from the MeOH/water mixture. The solid was filtered off, washed with MeOH/water (1:1) and hexane and dried under vacuum, to give a yellow solid (238 mg, 52.5%). MS: 367.0 [M]$^+$; $^1$H-NMR (D$_6$-DMSO): δ 8.63 (d, 1H), 8.29

(s, 1H), 8.18 (d, 1H), 8.00 (s, 1H), 7.49 (t, 1H), 7.40 (d, 1H), 7.15 (d, 1H), 4.95 (s, 1H), 1.04 (s, 9H).

Example 14

[2-(3-Chloro-phenyl)-6-trifluoromethyl-imidazo[1,2-a]pyridin-3-yl]-ethyl-amine

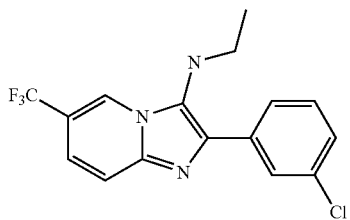 [SMILES: CCNc1c(-c2cccc(Cl)c2)nc2ccc(C(F)(F)F)cn12]

5-(trifluoromethyl)pyridin-2-amine (100 mg, 617 µmol, Eq: 1.00), 3-chlorobenzaldehyde (91.0 mg, 73.7 µl, 648 µmol, Eq: 1.05) and p-toluenesulfonic acid monohydrate (35.2 mg, 185 µmol, Eq: 0.3) were dissolved in MeOH (2.00 mL). The resulting colorless solution was stirred at rt. To this solution was added dropwise isocyanoethane (34.0 mg, 45.9 µl, 617 µmol, Eq: 1.00) and the corresponding yellow solution was stirred for 2 h. To the yellow clear solution was added dropwise water until the mixture got turbid and the product precipitated from the MeOH/water mixture. The solid was filtered off, washed with MeOH/water (1:1) and hexane and dried under vacuum, to give a yellow solid (111 mg, 53.0%). MS: 339.0 [M]$^+$; $^1$H-NMR (D$_6$-DMSO): δ 8.90 (s, 1H), 8.23 (s, 1H), 8.15 (d, 1H), 7.71 (d, 1H), 7.52 (t, 1H), 7.47-7.36 (m, 2H), 5.17 (t, 1H), 3.02 (m, 2H), 1.12 (t, 3H).

Example 15

[2-(3-Ethynyl-phenyl)-6-trifluoromethyl-imidazo[1,2-a]pyridin-3-yl]-isopropyl-amine

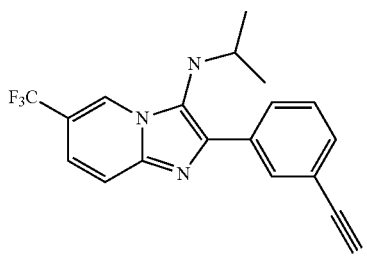 [SMILES: C#Cc1cccc(-c2nc3ccc(C(F)(F)F)cn3c2NC(C)C)c1]

5-(trifluoromethyl)pyridin-2-amine (100 mg, 617 µmol, Eq: 1.00), 3-ethynylbenzaldehyde (84.3 mg, 648 µmol, Eq: 1.05) and p-toluenesulfonic acid monohydrate (35.2 mg, 185 µmol, Eq: 0.3) were dissolved in MeOH (1.00 mL) and the intensive yellow solution was stirred for 5 min. To this yellow solution was added dropwise 2-isocyanopropane (42.6 mg, 58.2 µL, 617 µmol, Eq: 1.00) and the corresponding yellow solution was stirred for 2 h. Upon addition of water a yellow precipitate was formed. The solid was filtered off, washed with MeOH/water (1:1) and dried under vacuum to yield the product as a yellow solid (153 mg, 72.2%). MS: 344.0 [M+H]$^+$; $^1$H-NMR (D$_6$-DMSO): δ 8.90 (s, 1H), 8.36 (s, 1H), 8.25 (d, 1H), 7.71 (d, 1H), 7.50 (t, 1H), 7.46-7.39 (m, 2H), 5.10 (d, 1H), 4.24 (s, 1H), 3.25 (m, 1H), 1.08 (d, 6H).

Example 16

[2-(3-Chloro-phenyl)-6-trifluoromethyl-imidazo[1,2-a]pyridin-3-yl]-isopropyl-amine

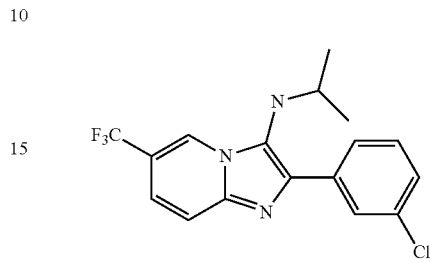

5-(trifluoromethyl)pyridin-2-amine (100 mg, 617 µmol, Eq: 1.00), 3-chlorobenzaldehyde (86.7 mg, 70.2 µl, 617 µmol, Eq: 1.00) and p-toluenesulfonic acid monohydrate (35.2 mg, 185 µmol, Eq: 0.3) were dissolved in MeOH (1.00 mL) and the intensive yellow solution was stirred for 5 min. To this yellow solution was added dropwise 2-isocyanopropane (42.6 mg, 58.2 µL, 617 µmol, Eq: 1.00) and the corresponding yellow solution was stirred for 90 min. To the yellow solution was added dropwise water and oil was formed. The water/MeOH was separated from the oil and the yellow oily residue was purified by flash column chromatography (40 g SiO$_2$, hexane/AcOEt 100:0 to 0:100) to yield a yellow solid (178 mg, 78.3%). MS: 354.0 [M+H]$^+$; $^1$H-NMR (D$_6$-DMSO): δ 8.92 (s, 1H), 8.29 (s, 1H), 8.19 (d, 1H), 7.72 (d, 1H), 7.51 (t, 1H), 7.47-7.36 (m, 2H), 5.13 (d, 1H), 3.26 (m, 1H), 1.08 (d, 6H).

Example 17

[2-(3-Bromo-phenyl)-6-trifluoromethyl-imidazo[1,2-a]pyridin-3-yl]-tert-butyl-amine

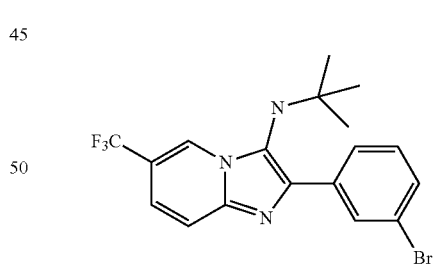

5-(trifluoromethyl)pyridin-2-amine (0.5 g, 3.08 mmol, Eq: 1.00), 3-bromobenzaldehyde (599 mg, 378 µL, 3.24 mmol, Eq: 1.05) and p-toluenesulfonic acid monohydrate (176 mg, 925 µmol, Eq: 0.3) were dissolved in MeOH (4 mL) and the intensive yellow solution was stirred for 10 min. To this yellow solution was added dropwise 2-isocyano-2-methyl-propane (256 mg, 351 µL, 3.08 mmol, Eq: 1.00) and the corresponding yellow solution was stirred for 14 h. The solvent was removed and the crude product was purified by flash column chromatography (hexane/AcOEt 100/0 to 0/100) to yield a light yellow solid (865 mg, 68.0%). MS: 414.0 [M+H]$^+$; $^1$H-NMR (D$_6$-DMSO): δ 8.90 (s, 1H), 8.48 (s, 1H), 8.26 (d, 1H), 7.72 (d, 1H), 7.53 (d, 1H), 7.46 (d, 1H), 7.40 (t, 1H), 4.96 (s, 1H), 1.05 (s, 9H).

Example 18

3-(3-tert-Butylamino-6-fluoro-imidazo[1,2-a]pyridin-2-yl)-benzonitrile

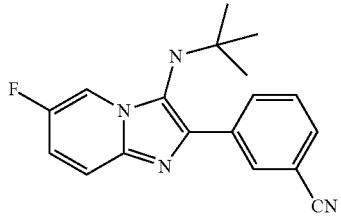 [SMILES: CC(C)(C)Nc1c(-c2cccc(C#N)c2)nc2ccc(F)cn12]

5-fluoropyridin-2-amine (200 mg, 1.78 mmol, Eq: 1.00), 3-formylbenzonitrile (246 mg, 1.87 mmol, Eq: 1.05) and p-toluenesulfonic acid monohydrate (102 mg, 535 µmol, Eq: 0.3) were dissolved in MeOH (2.00 mL) and the intensive yellow solution was stirred for 20 min. To this yellow solution was added dropwise 2-isocyano-2-methylpropane (148 mg, 203 µL, 1.78 mmol, Eq: 1.00) and the corresponding yellow solution was stirred for 1 h whereupon a white precipitate was formed. The precipitate was filtered off, washed with MeOH (4 mL) and dried under vacuum to give the product as an off-white solid (323 mg, 58.7%). MS: 308.0 $[M]^+$; $^1$H-NMR (CDCl$_3$): δ 8.35 (s, 1H), 8.26 (d, 1H), 8.14 (m, 1H), 7.63 (d, 1H), 7.60-7.52 (m, 2H), 7.13 (ddd, 1H), 3.01 (s, 1H), 1.10 (s, 9H).

Example 19

IC$_{50}$ Determinations of Exemplified Compounds

Dose Response Assay: ChanTest hTRPA1-CHO Stably Transfected Cell Line
Cell Culture and Assay Reagents:

| | |
|---|---|
| Ham's F12 | (GIBCO #11765-047) |
| Tetracycline-free Fetal Bovine Serum | (ClonTech#631106, Lot A301097018) |
| Blasticidin (10 mg/ml stock) | (GIBCO #A11139-02) |
| Zeocin (100 mg/ml stock) | (GIBCO #R250-01) |
| Doxycycline | (SIGMA #D9891) |
| Penicillin-Sprepromycin solution (100X) | (GIBCO #15140-122) |
| GlutaMAX (100X) | (GIBCO #35050) |
| Trypsin-EDTA | (GIBCO #25200-056) |
| PBS (without Calcium and Magnesium) | (GIBCO #14190) |
| HBSS | (GIBCO #14025) |
| Hepes | (GIBCO #15630) |
| BSA (fatty acid free, low endotoxin) | (SIGMA #A8806-5G) |
| DMSO | (SIGMA #D2650) |
| AP-18 | (SIGMA #A7232) |
| Cinnamaldehyde | (SIGMA #W228613) |
| ATP | (SIGMA #A-6419) |
| 2-Aminoethyl diphenylborinate | (SIGMA #D9754) |
| Menthol | (Sigma #M2772) |
| FLIPR Calcium 3 Assay Kit | (Molecular Devices #R8108) |
| Probenecid | (INVITROGEN #36400) |
| Plates | (BD #35-3962) |

CHO-K1 Tet-On HOMSA TRPA1 Clone 20
Chinese Hamster Ovary cells, inducible expression
Clone #20, received at passage #26
Channel expression in this cell line has been shown to be stable for at least 80 passages
Verified *Mycoplasma* free with MycoAlert Kit
Cell line expanded and banked
Growth Conditions:
Growth Media for CHO-K1 Tet-On HOMSA TRPA1 Clone 20
Ham's F-12 with 10% tetracycline-free FBS
1× penicillin-streptomycin
glutamax
0.01 mg/ml Blasticidin
0.40 mg/ml Zeocin
The cell line doubling rate was ~15 hours. The culture plates did not exceed 80% confluency.
To induce expression, tetracycline was added to blasticidin/zeocin-free media at a final concentration of 1 ug/ml. Experiments were run at 24 hours post induction.
Plating Conditions CHOK1/TRPA1 Cells:
Harvested cells with 0.025% trypsin/EDTA.
Resuspended cells in growth media without selection antibiotics.
Measured cell density and diluted to 2.4×10$^5$ cells/ml in media containing 1 ug/ml Doxycycline Plate 25 ul/well into 384 well black/clear tissue culture-treated plates.
Incubated overnight at 37° C.
Calcium Flux Assay:
Day of Assay:
Reagents:
Replacement Buffer: Hank's Balanced Salt Solution, 20 mM HEPES along with 0.005% BSA and 2× Probenecid
Dye Loading Buffer: Cal-3 NW Calcium dye was prepared by dissolving the contents of one vial with 500 ml Hank's Balanced Salt Solution containing 20 mM HEPES.
Control compounds for CHOK1/TRPA1 cells:
AP-18, stock 10 mM, prepare 3.5× compound dilution in a Compound Buffer (HBSS/20 mM HEPES/0.005% BSA)—final concentration 10 uM.
Preparation of Cinnamaldehyde (agonist addition):
FW=132.16
Specific gravity=1.046 gm/cc
1.32 gm/1.046 gm/cc=1.26 ml of stock
Add 1.74 ml DMSO=3.3 M stock
Working solution 4.5× (final 100 uM in Compound Buffer: HBSS/20 mM HEPES/0.005% BSA)
Compounds dilutions were prepared from 5 or 10 mM stock (100% DMSO):
Adjustments of volumes and concentrations were made at time of titration to reflect desired final assay concentrations.
Compounds were tested at either 20 µM three folds dilution 11 steps out or 30 µM two folds dilution 11 steps out.
3 µl of diluted compound were transferred into Weidmann 384-well plate in duplicates side-by-side.
Compound plates were resuspended with 100 ul of HBSS/20 mM HEPES/0.005% BSA buffer (Compound Buffer):
column 1A-H: buffer/DMSO (bk)
column 2A-H: AP-18 (control antagonist for CHOK1 TRPA1 cells)
column 1I-P: ATP (control for CHOK1 teton cells)
column 2 I-P: 2APB (control antagonist for CHOK1/TRPM8 cells).
Growth media was removed from the cell plates (20 ul) and 20 ul of the Replacement Buffer was added followed by addition of 25 ul of diluted dye. All three steps were performed using a Plate Washer BioTek 407. The plates were then incubated for 30' at RT.
After incubation, both the cell and compound plates were brought to the FLIPR and 20 ul of the diluted compounds/antagonist/bk were transferred to the cell plates by the FLIPR. Plates were then incubated for 30' at room temperature. After 30' incubation, plates were returned to the FLIPR and 20 ul of 4.5× Cinnamaldehyde was added to the cell plates. During the compound addition as well as agonist addition, fluorescence readings were taken simultaneously from all 384 wells of the cell plate every 1.5 seconds. Five readings were taken to establish a stable baseline, then 20 ul of sample was rapidly (30 ul/sec) and simultaneously added to each well of the cell plate. The fluorescence was continuously monitored before, during and after sample/agonist addition for a total elapsed time of 100 seconds (compound addition) and 120 seconds (agonist addition). Responses (increase in peak fluorescence) in each well following agonist addition was determined. The initial fluorescence reading from each well, prior to ligand stimulation, was used a zero baseline value for the data from that well. The responses were expressed as % inhibition of the inhibitor control as shown in Table 1 below:

TABLE 1

| Example | h-TRPA1 IC50 (µM) | Inhibition % @ concentration (µM) |
|---|---|---|
| 1 | 0.132 | 100% @ 1.0 |
| 2 | 0.195 | 100% @ 30 |
| 3 | 3.295 | 74.3% @ 30 |
| 4 | 1.326 | 100% @ 3.0 |
| 5 | 0.854 | 100% @ 30 |
| 6 | 2.133 | 90% @ 10.0 |
| 7 | 1.586 | 100% @ 10.0 |
| 8 | 1.086 | 100% @ 3.0 |
| 9 | 0.229 | 100% @ 30 |
| 10 | 0.221 | 100% @ 10.0 |
| 11 | 1.33 | 98% @ 30.0 |
| 12 | 0.110 | 100% @ 1.0 |
| 13 | 1.115 | 100% @ 30 |
| 14 | 2.067 | 100% @ 30 |
| 15 | 0.082 | 100% @ 10.0 |
| 16 | 0.143 | 100% @ 3.0 |
| 17 | 0.264 | 100% @ 10.0 |
| 18 | 20.42 | 80.9% @ 30 |

It is to be understood that the invention is not limited to the particular embodiments of the invention described above, as variations of the particular embodiments may be made and still fall within the scope of the appended claims.

The invention claimed is:

1. A compound of formula (I):

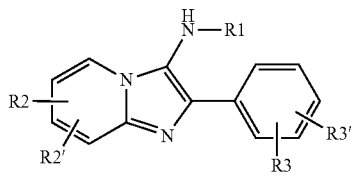

wherein R1 is cyclopropyl;
R2 and R2', independently of each other, are hydrogen, halogen, lower alkyl or lower haloalkyl, and
R3 and R3', independently of each other, are hydrogen, halogen, cyano or ethynyl,
or a pharmaceutically acceptable salt thereof.

2. A compound according to 1, wherein R2 and R2', independently of each other, are hydrogen, bromine, chlorine, fluorine, —$CF_3$ or methyl.

3. A compound according to claim 1, wherein one of R2 or R2' is hydrogen and the other is bromine, chlorine, fluorine, —$CF_3$ or methyl.

4. A compound according to claim 1, wherein R3 and R3', independently of each other, are hydrogen, bromine, chlorine, fluorine, cyano or ethynyl.

5. The compound according to claim 1, wherein one of R3 or R3' is hydrogen and the other is bromine, chlorine, fluorine, cyano or ethynyl.

6. A compound selected from
6-Bromo-2-(3-chloro-phenyl)-imidazo[1,2-a]pyridin-3-yl]-isopropyl-amine;
[6-Chloro-2-(3-chloro-phenyl)-imidazo[1,2-a]pyridin-3-yl]-isopropyl-amine;
[6-Fluoro-2-(3-fluoro-phenyl)-imidazo[1,2-a]pyridin-3-ylamino]-acetic acid methyl ester;
tert-Butyl-[2-(3-fluoro-phenyl)-6-trifluoromethyl-imidazo[1,2-a]pyridin-3-yl]-amine;
3-(3-tert-Butylamino-6-trifluoromethyl-imidazo[1,2-a]pyridin-2-yl)-benzonitrile;
3-(3-tert-Butylamino-6-chloro-imidazo[1,2-a]pyridin-2-yl)-benzonitrile;
[6-Chloro-2-(3-chloro-phenyl)-imidazo[1,2-a]pyridin-3-yl]-cyclopropyl-amine;
[8-Bromo-6-chloro-2-(3-chloro-phenyl)-imidazo[1,2-a]pyridin-3-yl]-tert-butyl-amine;
[6-Bromo-2-(3-chloro-phenyl)-7-methyl-imidazo[1,2-a]pyridin-3-yl]-tert-butyl-amine;
[6-Bromo-2-(3-chloro-phenyl)-8-methyl-imidazo[1,2-a]pyridin-3-yl]-tert-butyl-amine;
tert-Butyl-[2-(3,5-dichloro-phenyl)-6-trifluoromethyl-imidazo[1,2-a]pyridin-3-yl]-amine;
tert-Butyl-[2-(3-ethynyl-phenyl)-6-trifluoromethyl-imidazo[1,2-a]pyridin-3-yl]-amine;
tert-Butyl-[2-(3-chloro-phenyl)-7-trifluoromethyl-imidazo[1,2-a]pyridin-3-yl]-amine;
[2-(3-Chloro-phenyl)-6-trifluoromethyl-imidazo[1,2-a]pyridin-3-yl]-ethyl-amine;
[2-(3-Ethynyl-phenyl)-6-trifluoromethyl-imidazo[1,2-a]pyridin-3-yl]-isopropyl-amine;
[2-(3-Chloro-phenyl)-6-trifluoromethyl-imidazo[1,2-a]pyridin-3-yl]-isopropyl-amine;
[2-(3-Bromo-phenyl)-6-trifluoromethyl-imidazo[1,2-a]pyridin-3-yl]-tert-butyl-amine; and
3-(3-tert-Butylamino-6-fluoro-imidazo[1,2-a]pyridin-2-yl)-benzonitrile.

7. A compound selected from
6-Bromo-2-(3-chloro-phenyl)-imidazo[1,2-a]pyridin-3-yl]-isopropyl-amine;
[6-Chloro-2-(3-chloro-phenyl)-imidazo[1,2-a]pyridin-3-yl]-isopropyl-amine;
tert-Butyl-[2-(3-ethynyl-phenyl)-6-trifluoromethyl-imidazo[1,2-a]pyridin-3-yl]-amine;
[2-(3-Ethynyl-phenyl)-6-trifluoromethyl-imidazo[1,2-a]pyridin-3-yl]-isopropyl-amine; and
[2-(3-Chloro-phenyl)-6-trifluoromethyl-imidazo[1,2-a]pyridin-3-yl]-isopropyl-amine.

8. A pharmaceutical composition comprising a therapeutically effective amount of a compound according to any one of claim 1, 6, or 7 and a pharmaceutically acceptable carrier.

* * * * *